US00PP20491P2

(12) United States Plant Patent
Striem

(10) Patent No.: US PP20,491 P2
(45) Date of Patent: Nov. 17, 2009

(54) GRAPEVINE PLANT NAMED 'SUGRATHIRTYFIVE'

(50) Latin Name: *Vitis vinifera*
Varietal Denomination: Sugrathirtyfive

(75) Inventor: Michael J. Striem, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 12/287,458

(22) Filed: Oct. 8, 2008

(51) Int. Cl.
*A01H 5/00* (2006.01)

(52) U.S. Cl. ..... Plt./207

(58) Field of Classification Search ..... Plt./207
See application file for complete search history.

(56) References Cited

U.S. PATENT DOCUMENTS

| | | | |
|---|---|---|---|
| PP3,106 | P | 4/1972 | Garabedian |
| PP11,820 | P2 | 3/2001 | Cain |
| PP19,065 | P3 | 8/2008 | Cain et al. |

*Primary Examiner*—Kent L Bell
(74) *Attorney, Agent, or Firm*—Knobbe, Martens, Olson & Bear LLP

(57) ABSTRACT

A new and distinct grapevine plant variety characterized by producing late ripening, naturally large, firm, round berries with creamy berry skin. The berries have high sugar content, a crunchy bite, and a mild, sweet Muscat flavor.

1 Drawing Sheet

Latin name of the genus and species claimed: *Vitis vinifera*. Variety denomination: 'Sugrathirtyfive'.

BACKGROUND AND SUMMARY OF THE INVENTION

This invention relates to the discovery and asexual propagation of a new and distinct variety of grapevine as herein described and illustrated. The new variety was first hybridized by Michael Striem in Wasco, Kern County, Calif., the variety being originated by controlled hybridization and subsequent culture of seed traces and embryo rescue procedures.

The new variety 'Sugrathirtyfive' is characterized by producing late ripening, naturally large, firm, round berries with creamy berry skin. The berries of 'Sugrathirtyfive' have high sugar content, a crunchy bite, and a mild, sweet Muscat flavor. A cluster of 'Sugrathirtyfive' fruit has good attachment, but is not as compact as those of other comparable varieties.

The seed parent is the varietal selection '97148-027-365' (unpatented) and the pollen parent is the varietal selection '99080-126-251' (U.S. Plant Pat. No. 19,065), otherwise known as 'Sugrathirtyone'. The parent varieties were first crossed in May 2004, by Michael Striem. From the initial population of hybrid ovules, embryo rescue methods were used to produce a population from which the present variety was selected. The date of first sowing was July 2004, and the date of first flowering was May 2006.

The new variety 'Sugrathirtyfive' was first asexually propagated in December 2006, in Wasco, Kern County, Calif., by Michael Striem using hardwood cuttings. The new variety 'Sugrathirtyfive' resembles its seed parent '97148-027-365' (unpatented) in many characteristics, such as the same creamy color type with the same type of cluster structure, but differs from its seed parent in that it has larger, more uniform, and rounder berries. Additionally, 'Sugrathirtyfive' is more productive and less vigorous than its seed parent and ripens about a week later with a higher sugar content of about 19 Brix.

The new variety 'Sugrathirtyfive' resembles its pollen parent '99080-126-251' (U.S. Plant Pat. No. 19,065), otherwise known as 'Sugrathirtyone', in many characteristics, such as the same firmness and crunchy bite and with uniform creamy berry skin finish. Additionally, similar to its pollen parent, 'Sugrathirtyfive' has a good attachment of the berries. Unlike its pollen parent, the skin of the fruit is thinner. 'Sugrathirtyfive' has a more uniform and rounder berry shape than its pollen parent with a mild muscat flavor. The new variety also differs from its pollen parent 'Sugrathirtyone' in that the berries of the pollen parent are much smaller (3.6 gr.) whereas those of the new variety 'Sugrathirtyfive' are larger (6.8 gr.). Additionally, 'Sugrathirtyfive' ripens approximately two weeks before the pollen parent.

The new variety 'Sugrathirtyfive' ripens late in the season, about seven weeks after 'Sugraone' (U.S. Plant Pat. No. 3,106) and about a month after 'Thompson Seedless' (unpatented).

The new variety 'Sugrathirtyfive' resembles the comparable variety U.S. Plant Pat. No. 11,820, otherwise known as 'Sugraeighteen', in its sweet muscat flavor. However, 'Sugrathirtyfive' develops a firmer berry with a more crunchy bite than 'Sugraeighteen'. The berries of 'Sugrathirtyfive' are naturally larger (6.8 gr. vs. 3.7 gr.) and ripen two weeks later. A cluster of 'Sugrathirtyfive' is not as compact as those of 'Sugraeighteen'.

The new variety 'Sugrathirtyfive' differs from the comparable variety 'Thompson Seedless' (unpatented) in that 'Sugrathirtyfive' is more productive, has a larger natural berry size (6.8 gr. vs. 2.5 gr. of the natural performance) and ripens about a month later. In addition, the berries of 'Sugrathirtyfive' are firmer and have better attachment to the cluster's stem.

The new 'Sugrathirtyfive' variety has been shown to maintain its distinguishing characteristics through successive asexual propagations by, for example, cuttings.

Variations of the usual magnitude from the described above may occur with changes in growing conditions, irrigation, fertilization, pruning, management and climatic variations.

BRIEF DESCRIPTION OF THE DRAWINGS

The accompanying drawing in FIG. 1 illustrates in full color a typical cluster of berries, a young shoot, and a mature leaf blade of the new grapevine. The colors are as nearly true as is reasonably possible in a color representation of this type.

DETAILED DESCRIPTION OF THE PREFERRED EMBODIMENT

Figure 1:
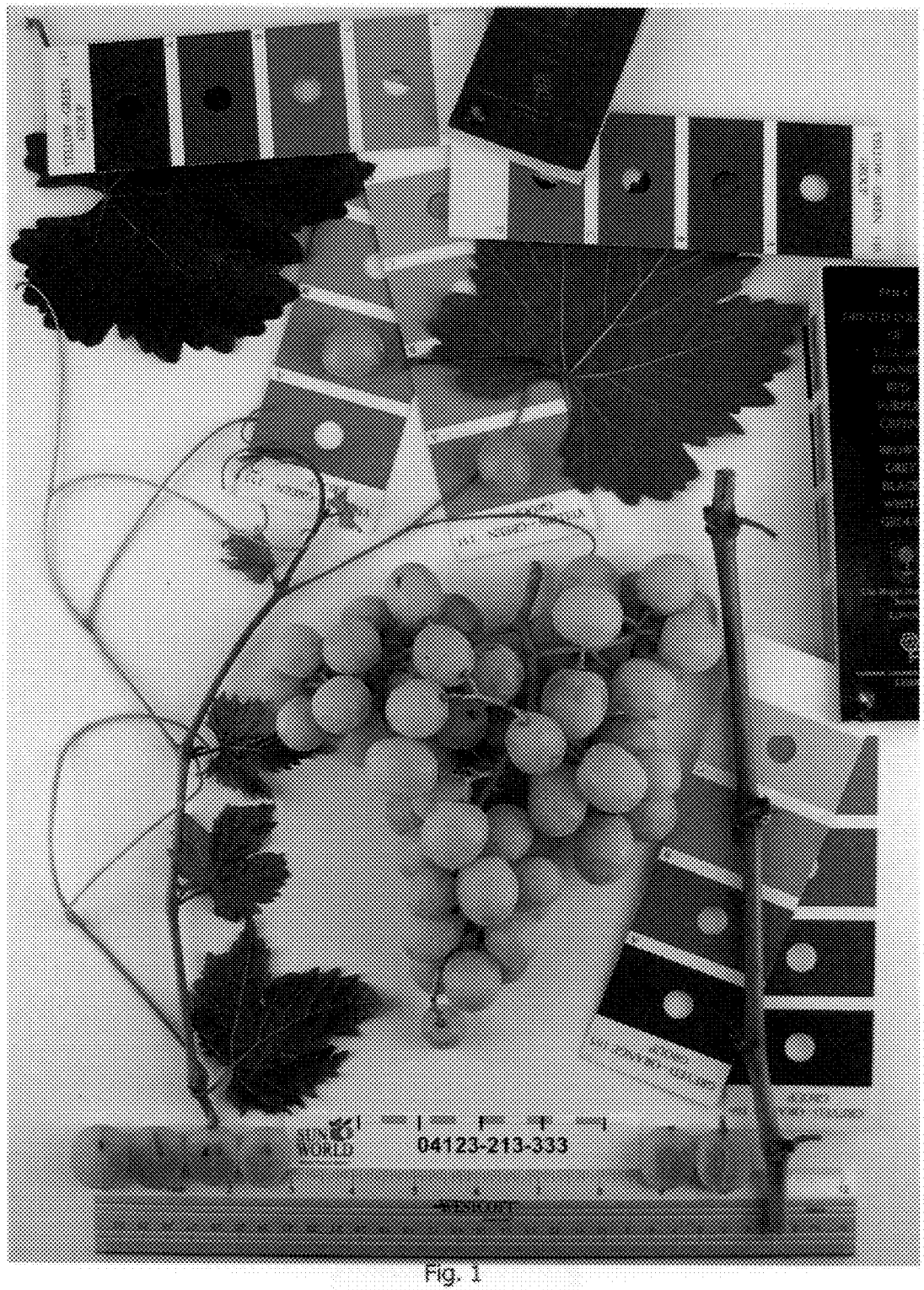

Throughout this specification, color names beginning with a small letter signify that the name of that color, as used in common speech, is aptly descriptive. Color names beginning with a capital letter designate values based upon the R.H.S. Colour Chart, published by The Royal Horticultural Society, London, England.

Many of the description values in this specification are based on and conform to those set forth by the International Board for Plant Genetic Resources Institute Grape Descriptors (*Vitis* spp.) of 1983 and/or 1997 which was developed in collaboration with the Office International de la Vigne et du Vin (OIV) and the International Union for the Protection of New Varieties of Plants (UPOV).

The descriptive matter which follows pertains to 'Sugrathirtyfive' plants grown in the vicinity of Wasco, Kern County, Calif., during 2007 and 2008, and is believed to apply to plants of the variety grown under similar conditions of soil and climate elsewhere.

VINE

General:

*Planting.*—Trained to a modified gable trellis, planted in a 7 ft.×12 ft. spacing.

*Practices.*—Gene-pool-vine: Cane pruned to approximately 6 canes per vine, 3 spurs per vine. Test-vines: Cane pruned to approximately 12 to approximately 18 two-bud-spurs per vine, and tested also as cane pruned to approximately 6 canes per vine, 6–8 buds per cane.

*Size.*—Medium. Height: Approximately 2.0 m. Width: Approximately 2.2 m.

*Vigor.*—Medium.

*Fresh pruning weight.*—Approximately 1.9 kg per vine.

*Density of foliage.*—Medium.

*Productivity.*—Productive — approximately 20 clusters per vine.

*Yield.*—Approximately 12.240 kg per vine, thinned to approximately 20 clusters per vine.

*Crop load.*—Approximately 6.4 kg per vine (kg fruit per kg fresh-pruning-weight).

*Rootstock.*—Not applicable.

*Own root.*—Yes.

*Resistance.*—Neither resistance nor susceptibility to diseases or pests has been observed in this variety.

Trunk:

*Shape.*—Medium.

*Diameter.*—Approximately 42 mm.

*Straps.*—Short.

*Surface texture.*—Shaggy.

*Inner bark color.*—Near Dark Grey Orange 165A.

*Outer bark color.*—Near Grey 201A.

SHOOTS

Young shoot:

*Form of tip.*—Wide open.

*Distribution of anthocyanin coloration of tip.*—Absent.

*Intensity of anthocyanin coloration of tip.*—Absent.

*Density of prostrate hairs on tip.*—Absent.

*Density of erect hairs on tip.*—Absent.

Woody shoot (mature canes):

*Shape.*—Slender.

*Internode length.*—Approximately 63.3 mm.

*Width at node.*—Approximately 8.2 mm.

*Cross section.*—Circular.

*Surface.*—Smooth.

*Main color.*—Light Brown 166A+165B.

*Lenticels.*—Absent.

*Density of erect hairs on nodes.*—Absent or Very Sparse.

*Density of erect hairs on internodes.*—Absent or Very Sparse.

*Growth of auxiliary shoots.*—Medium.

Flowering shoot:

*Vigor during flowering.*—Weak.

*Attitude during flowering on shoots which are not tied.*—Semi-erect.

*Color of dorsal side of internodes.*—Near Medium Yellow Green 144A.

*Color of ventral side of internodes.*—Near Medium Yellow Green 144B.

*Color of dorsal side of nodes.*—Near Medium Yellow Green 144B.

*Color of ventral side of nodes.*—Near Medium Yellow Green 144B.

*Density of erect hairs on nodes.*—Absent.

*Erect hairs on internode.*—Absent.

*Density of prostrate hairs on nodes.*—Absent.

*Density of prostrate hairs on internodes.*—Absent.

*Anthocyanin coloration of buds.*—Weak.

Tendrils:

*Distribution on the shoot at full flowering.*—Discontinuous.

*Thickness.*—Thin.

*Color.*—Near Light Yellow Green 145A.

*Form.*—Bifurcated.

*Number of consecutive tendrils.*—Up to 2.

*Length of tendril.*—Short, approximately 16.5 cm.

LEAVES

Young leaves:

*Color of upper surface of first 4 distal unfolded leaves.*—Copper.

*Average intensity of anthocyanin coloration of six distal leaves prior to flowering.*—Absent.

*Density of prostrate hairs between veins at lower surface of 4th distal unfolded leaf.*—Absent.

*Density of erect hairs between veins at lower surface of 4th distal unfolded leaf.*—Absent.

*Density of prostrate hairs on veins at lower surface of 4th distal unfolded leaf.*—Absent.

*Density of erect hairs on veins at lower surface of 4th distal unfolded leaf.*—Absent.

Mature leaves:
*Average length.*—Approximately 120.6 mm.
*Average width.*—Approximately 147.0 mm.
*Size of blade.*—Medium.
*Shape of blade.*—Pentagonal.
*Number of lobes.*—5.
*Anthocyanin coloration of main veins on the upper side of the blade.*—Absent.
*Mature leaf profile.*—Flat.
*Blistering surface of blade upper surface.*—Very Weak.
*Leaf blade tip.*—In the plane of the leaf.
*Undulation of margin.*—Slight.
*Thickness.*—Medium.
*Undulation of blade between main and lateral veins.*—Absent.
*Shape of teeth.*—Convex on both sides.
*Length of teeth.*—Medium.
*Ratio length/width of teeth.*—Medium.
*General shape of petiole sinus.*—Wide open.
*Tooth at petiole sinus.*—Absent.
*Petiole sinus limited by veins.*—Absent.
*Shape of upper lateral sinus.*—Open.
*Depth of upper lateral sinus.*—Very Shallow.
*Density of prostrate hairs between veins on lower surface of blade.*—Absent.
*Density of erect hairs between veins on lower surface of blade.*—Absent.
*Density of prostrate hairs on main veins on lower surface of blade.*—Absent.
*Density of erect hairs on main veins on lower surface of blade.*—Absent.
*Density of prostrate hairs on main veins on upper surface of blade.*—Absent.
*Autumn coloration of leaves.*—Yellow, 162C.

Upper surface:
*Color.*—Near Dark Yellow Green 147A.
*Surface texture.*—Smooth.
*Surface appearance.*—Dull.
*Glossiness.*—Weak.
*Pubescence.*—Absent.

Lower surface:
*Color.*—Medium Yellow Green 146B.
*Anthocyanin coloration of main veins on lower leaf surface.*—Absent.
*Glossiness.*—Weak.
*Pubescence.*—Absent.
*Surface texture.*—Smooth.
*Surface appearance.*—Dull.

Petiole:
*Length of petiole.*—Medium, approximately 7.7 cm.
*Length of petiole compared to middle vein.*—Slightly shorter.
*Diameter.*—Approximately 3 mm.
*Density of prostrate hairs on petiole.*—Absent.
*Density of erect hairs on petiole.*—Absent.
*Shape of base of petiole sinus.*—V-shaped.
*Color.*—Striped Yellow Green 144B+Red 183C.

Buds:
*Shape.*—Pointed.
*Size.*—Medium, approximately 5 mm×5mm.
*Position.*—Markedly held out.
*Cane bud fruitfulness.*—Basal most fruitful.
*Time of bud burst.*—Medium.

FLOWERS

General:
*Flower sex.*—Hermaphrodite.
*Length of first inflorescence.*—Medium, approximately 23.6 cm.
*Position of first flowering node.*—Third node.
*Number of inflorescences per shoot.*—1.1 to 2.
*Date of full bloom.*—May 5th.
*Time of bloom.*—Medium.
*Size (diameter of fully open flower).*—Medium, approximately 5 mm.

FRUIT

General:
*Ripening period.*—Late, August 25.
*Use.*—Table grapes.
*Keeping quality.*—Good.
*Shipping quality.*—Good.
*Date of first harvest.*—Aug. 25, 2006.
*Solids-sugar.*—Medium.
*Refractometer test.*—Approximately 19.3%.
*Acid.*—Medium, approximately 3 gr./L tartaric acid.
*Juice pH.*—Approximately 4.0.

Cluster:
*Bunch size (peduncle excluded).*—Medium.
*Bunch length (peduncle excluded).*—Medium, approximately 24.3 cm.
*Bunch width.*—Approximately 13.0 cm.
*Bunch weight.*—Medium, approximately 442.6 g.
*Bunch density.*—Medium.
*Number of berries.*—Approximately 61.6.
*Form.*—Conical.

Peduncle:
*Length of peduncle.*—Medium, approximately 13.2 mm.
*Lignification of peduncle.*—Medium.
*Color.*—Near Medium Yellow Green 144A.

Berry:
*Size.*—Large.
*Uniformity of size.*—Uniform.
*Berry weight.*—Heavy, approximately 6.8 gr.
*Shape.*—Broad to Short Elliptic.
*Presence of seeds.*—Rudimentary.
*Cross section.*—Circular.
*Dimensions.*—Longitudinal axis: Approximately 23.3 mm. Horizontal axis: Approximately 28.2 mm.
*Skin color (without bloom).*—Yellow-green 151A+153C.
*Juiciness of flesh.*—Slightly juicy.
*Berry firmness.*—Very Firm.
*Particular flavor.*—Muscat.
*Bloom (cuticular wax).*—Weak.
*Pedicel length.*—Medium, approximately 8.5 mm.
*Berry separation from pedicel.*—Medium.
*Visibility of hilum.*—Slightly.

Skin:
*Thickness.*—Medium.
*Texture.*—Smooth.
*Reticulation.*—Absent.
*Roughness.*—Absent.
*Tenacity.*—Tenacious to flesh.

Seed:

*Number of seeds per berry.*—Approximately 2.3.

*Size.*—Small.

*Color.*—Light Brown.

*Texture.*—Medium.

*Endosperm.*—Absent.

*Fresh weight of seed-traces/berry.*—Approximately 14.5 mg.

*Room-dry weight of seed-traces/berry.*—Approximately 10.3 mg.

What is claimed is:

1. A new and distinct variety of grapevine plant as herein illustrated and described.

* * * * *